United States Patent [19]

Bhattacharjee

[11] Patent Number: 4,917,503

[45] Date of Patent: Apr. 17, 1990

[54] PHOTOACTIVATABLE LEUCO BASE TIME-TEMPERATURE INDICATOR

[75] Inventor: Himangshu R. Bhattacharjee, Randolph, N.J.

[73] Assignee: LifeLines Technology, Inc., Morris Plains, N.J.

[21] Appl. No.: 103,418

[22] Filed: Sep. 30, 1987

Related U.S. Application Data

[63] Continuation of Ser. No. 803,750, Dec. 2, 1985, abandoned.

[51] Int. Cl.$^4$ .................. G01K 3/04; G01K 11/12
[52] U.S. Cl. .................. 374/102; 116/206; 116/207; 252/962; 374/162; 426/88; 436/905
[58] Field of Search .................. 116/206, 207, 216; 252/408.1, 586, 962, 963; 374/102, 106, 161, 162; 422/56-58, 86; 426/88; 428/913; 430/338, 344, 346; 436/2, 902, 904, 905

[56] References Cited

U.S. PATENT DOCUMENTS

| | | |
|---|---|---|
| 2,936,276 | 5/1960 | Chalkley .................. 436/2 |
| 3,525,616 | 8/1970 | Hackmann et al. .................. 430/270 |
| 3,768,976 | 10/1973 | Hu et al. .................. 116/207 |
| 3,954,475 | 5/1976 | Bonham et al. .................. 430/281 |
| 3,966,414 | 6/1976 | Khattab et al. .................. 116/207 |
| 4,022,617 | 5/1977 | McGuckin .................. 430/351 |
| 4,039,332 | 8/1977 | Kokelenberg et al. .................. 430/337 |
| 4,189,399 | 2/1980 | Patel .................. 252/408.1 |
| 4,205,043 | 5/1980 | Esch et al. .................. 422/56 |
| 4,208,186 | 6/1980 | Patel .................. 23/230 |
| 4,212,153 | 7/1980 | Kyonieus et al. .................. 368/88 |
| 4,276,190 | 6/1981 | Patel .................. 252/408.1 |
| 4,373,032 | 2/1983 | Preziozi et al. .................. 521/38 |
| 4,466,941 | 8/1984 | Cerami et al. .................. 422/57 |
| 4,594,307 | 6/1986 | Ishida .................. 430/203 |

FOREIGN PATENT DOCUMENTS

| | | | |
|---|---|---|---|
| 0117390 | 9/1984 | European Pat. Off. .................. | 116/206 |
| 2752 | 3/1963 | Japan .................. | 426/88 |
| 2753 | 3/1963 | Japan .................. | 426/88 |
| 1161058 | 8/1969 | United Kingdom . | |

OTHER PUBLICATIONS

Richard Seltzer, "Indicator for perishable products developed", C & EN, 9-29-86.
J. V. Crivello, Polymer Eng. & Sci. 23,953, (1983).
J. V. Crivello et al., J. Polymer Sci., Symposium Nw. 56,383, (1976).
S. Maslowski, Appl. Optics 13,857, (1974).
Shelf Life Estimation of Beverage and Food Products using Bar Coded Time-Temperature Indicator Labels.
H. R. Bhattacharjee—Photoactivatable Time-Temperature Indicators for Low-Temperature Applications, J. of Agricultural and Food Chemistry, vol. 36, pp. 525-529.

Primary Examiner—William A. Cuchlinski, Jr.
Assistant Examiner—W. Morris Worth
Attorney, Agent, or Firm—Arthur J. Plantamura

[57] ABSTRACT

A photoactivated time-temperature indicator is based on a leuco base system. A thermally insensitive, white ("inactive") leuco base (or a mixture of such leuco bases) is mixed, preferably in a polymeric matrix, with a material that generates acid upon exposure to light. Photoexcitation, preferably by UV or near UV light, causes the formation of a thermally sensitive, color-forming ("active") product. Following this activation step, a progressive color development occurs at a rate that increases with temperature. The indicator is useful for monitoring the freshness of perishable products, particularly those stored at subambient temperature.

17 Claims, 2 Drawing Sheets

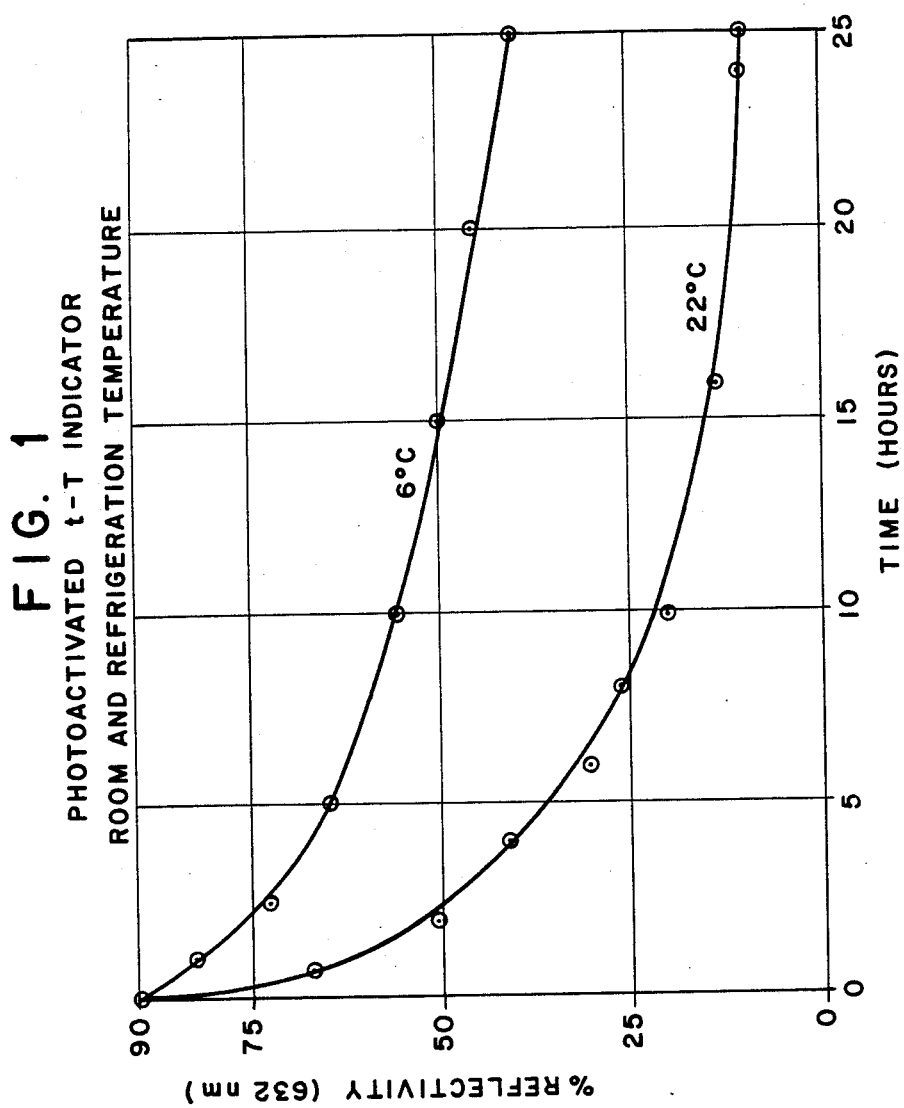

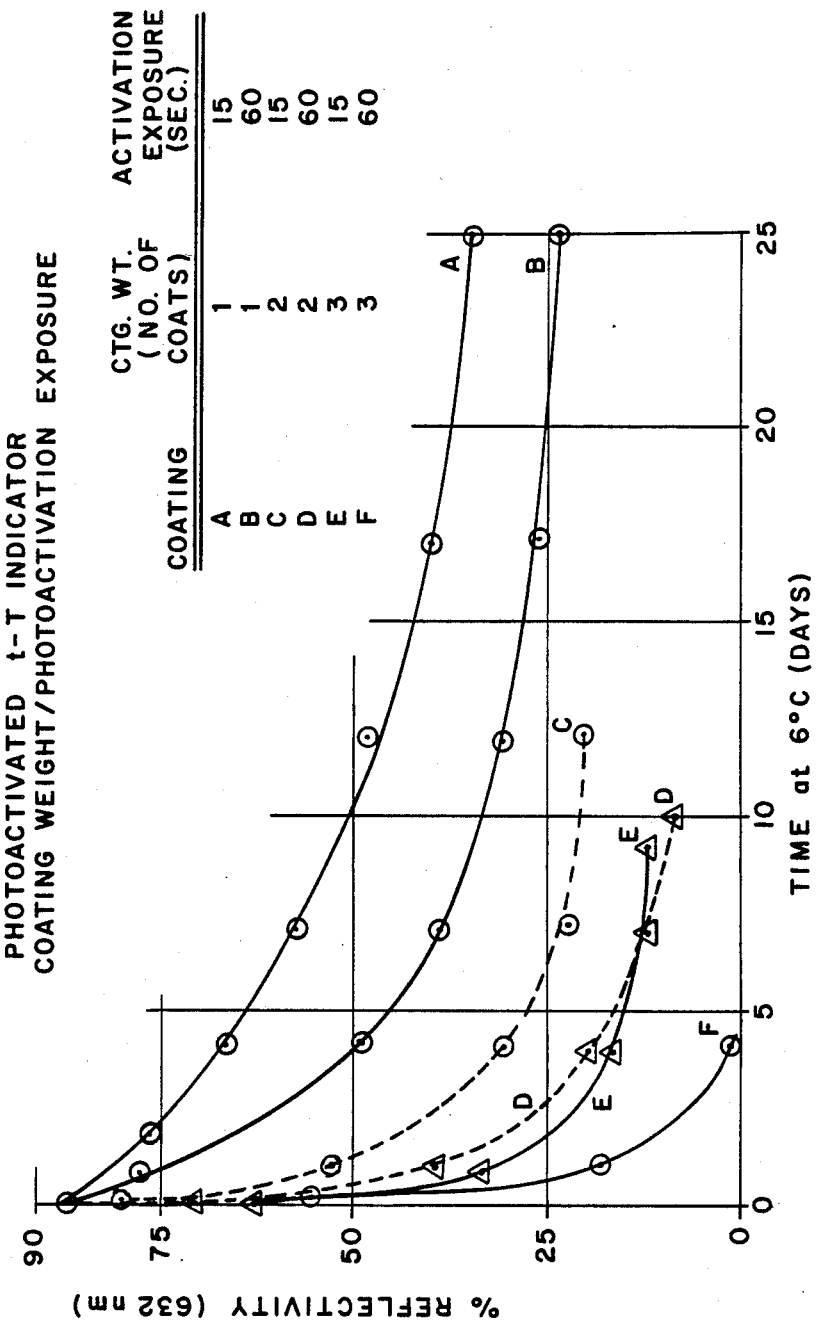

PHOTOACTIVATABLE LEUCO BASE TIME-TEMPERATURE INDICATOR

This application is a continuation of application Ser. No. 803,750, filed Dec. 2, 1985, now abandoned.

BACKGROUND OF THE INVENTION

1. Field of the Invention

This invention relates to a time-temperature indicator and, more particularly, to an indicator that is inactive until it is activated by actinic radiation.

2. Description of the Prior Art

Several patents have disclosed the use of color-changing indicators to monitor the time-temperature history of perishables. Among these are U.S. Pat. No. 4,189,399, issued Feb. 19, 1980, to Patel; and U.S. Pat. No. 4,212,153, issued July 15, 1980, to Kydonieus et al.

When the perishable to be monitored has a short useful lifetime and/or requires refrigeration, then it is desirable, if not essential, to use an indicator that is inactive untial activated. Patel, U.S. Pat. Nos. 4,208,186, issued June 17, 1980, and 4,276,190, issued June 30, 1981, disclosed diacetylenic compositions having an inactive form that is activated by contact with an activating vapor. Activation of a diacetylenic monomer in salt form by conversion to the acid form was disclosed in U.S. Pat. No. 4,373,032, issued Feb. 9, 1983, to Preziosi et al.

U.S. Pat. No. 3,768,976, issued Oct. 30, 1973, to Hu et al., has disclosed a temperature-time integrating indicator that is based on temperature-dependent oxygen diffusion into a package that includes an aqueous solution of a redox dye. The dye is dark in the reduced state and becomes colorless when it is oxidized. A similar indicator, involving a free radical sensitive dye and a peroxide on a carrier, was disclosed in U.S. Pat. No. 3,966,414, issued June 29, 1976, to Khattab et al.

Photoactivation of a variety of chemical processes has been reported. It is known, for example, that certain onium salts are photoinitiators of cationic polymerization (see, e.g., J. V. Crivello, Polymer Eng. and Sci. 23, 953 (1983); and J. V. Crivello et al., J. Polymer Sci., Symposium No. 56, 383 (1976)).

Photogeneration of a hydrohalic acid has been disclosed by S. Maslowski, Appl. Optics 13, 857 (1974) and in U.S. Pat. No. 4,247,611, issued Jan. 27, 1981, to Sander et al.

SUMMARY OF THE INVENTION

In accordance with the present invention, a photoactivatable time-temperature indicator comprises a mixture of:

(a) a thermally inactive compound that comprises a leuco base and (b) a photosensitive compound that, on exposure to actinic radiation, forms an acid that converts the leuco base to a thermally active product. Preferably, the mixture is dispersed in a medium and coated onto a substrate.

In operation, the present invention provides a method of measuring an incremental time-temperature exposure, which comprises the steps:

(a) exposing the photoactivatable indicator described above to actinic radiation to render it thermally active, (b) measuring the reflectivity of the indicator at a specified wavelength, (c) measuring the reflectivity of the indicator at the specified wavelength after the incremental time-temperature exposure, and (d) calculating the incremental time-temperature exposure by using a pre-established relationship between a change in reflectivity of the indicator and time-temperature exposure. The process is particularly useful for measuring the exposure of a perishable article, which involves first applying to the article a photoactivatable time-temperature indicator and then following the steps set forth above.

The term "time-temperature indicator," as it is used in the present specification and claims, refers to a composition that responds in a measurable and predictable way to the integrated effect of time and temperature. The activation of the time-temperature indicators of this invention is by photogeneration of an "acid," which term is understood to include Lewis acids, Bronsted acids, and the like.

BRIEF DESCRIPTION OF THE DRAWINGS

FIG. 1 depicts the time dependence of reflectivity at 632 nm of an activated indicator label of the present invention held at room temperature and at 6° C.

FIG. 2 depicts the time dependence of the rate of change of reflectivity on indicator coating thickness and photoactivation.

DETAILED DESCRIPTION OF THE INVENTION

Many articles of commerce—both food and nonfood—are perishable. Particularly when the perishable is enclosed in packaging, it may not be readily apparent when the article has exceeded its useful lifetime. It is even more difficult to determine precisely where an article is positioned on an imaginary graph that plots its deterioration as a function of time. Since the rate at which a perishable deteriorates is generally a function of its integrated time-temperature exposure—at least within a restricted range of time-temperature—a time-temperature indicator is a useful tool for those who are concerned with the freshness of perishable products. The indicator must comprise a composition that provides a readily-measurable physical property that changes in a reproducible way with exposure to time-temperature. For convenience, we use color, but other properties are also suitable. For a real-time indicator, the time frame over which the color changes, in the temperature range of interest, must correspond to that over which the perishable product deteriorates.

For products that undergo significant changes over relatively short times (a few days, for example) or at relatively low temperatures (zero degrees Celsius or below, for example) some form of controlled activation is required to assure that color change does not begin until the desired point in time. One possible means of activation is with light or "photoactivation." Potential advantages of photoactivation include (i) activation of color change at a specified point in time, (ii) totally non-intrusive nature of activation process, and (iii) possibility of controlling extent of activation by photodose, thereby providing a range of time-temperature characteristics with a single indicator.

Some disadvantages or concerns include (i) possibility of activation by ambient light exposure, (ii) potential difficulties in reproducing activation dose, and (iii) possible acceleration of color change due to activating radiation.

A suitable time-temperature indicator can be based on color development of a leuco base. Leuco bases are the colorless (i.e., white) forms, and can be considered to be the precursors, of dyes such as diphenylmethane and triarylmethane dyes. (Detailed information concerning these dyes—preparation, properties, etc.—appears in K. Venkataraman, *The Chemistry of Synthetic Dyes*, Vol. II, Academic Press, N.Y., 1952, pp 705 ff.)

For the present invention, triarylmethane leuco bases (I) are generally preferred:

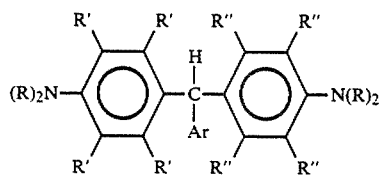

Each R is independently H,(C$_1$-C$_2$)alkyl, hydroxyalkyl, sulfonated alkyl, or a substituted phenyl group. Each R' is independently H,C$_1$-alkyl, or a sulfite group. Each R" is independently H or C$_1$-alkyl. Ar is

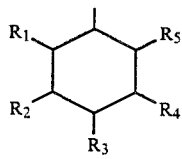

where R$_1$-R$_5$ are independently H,(C$_1$-C$_4$)alkyl, halogen, amine, N(C$_1$-C$_4$)alkyl, carboxylic acid, sulfite, hydroxyl, or a substituted phenyl group. Ar may also be replaced by naphthalene or substituted naphthalenes, in which case the leuco base is a diphenylnaphthylmethane leuco.

A He-Ne laser, which emits at 632 nm, is a convenient light source for monitoring the reflectivity of the indicators of the present invention. When that laser is used, the preferred leuco bases are those that provide final colors green, blue, or violet. Specifically, malachite green leuco (II), brilliant green leuco (III), and crystal violet leuco (IV) are particularly preferred.

By selecting from among these and other suitable leuco bases, as well as mixtures of two or more of them, a wide variety of desired colors can be obtained.

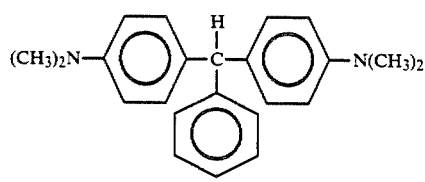

II

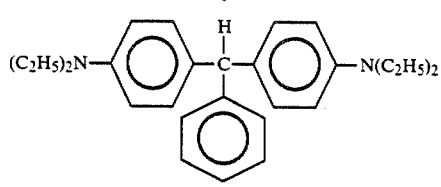

III

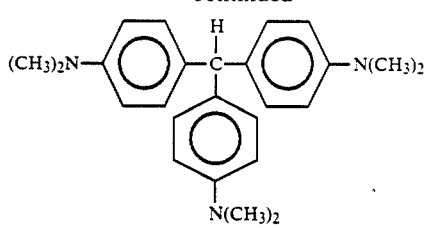

IV

It is known that colorless leuco base is converted to dye in the two-step process shown below:

(1) leuco base (2) carbinol carbinol dye where HY is an acid. Surprisingly, if a mixture of leuco base and photoacid is exposed to actinic radiation, the rate at which color develops depends on the temperature; i.e., the color development is an indication of time-temperature exposure. Although we don't know the mechanism that underlies this effect, it may be that the photoactivation process generates a carbinol or carbinol equivalent that then reacts with the photoacid to start the development of color. For simplicity, in the description of this process, we refer to the dye being formed by the (time-temperature dependent) action of photoacid on the leuco base.

A number of chemical compounds are known to generate acids upon excitation with actinic radiation. Among these photoacids are o-nitrobenzaldehydes and substituted o-nitrobenzaldehydes; trihaloalcohols ($X_3ROH$, where X is a halogen and R is an alkyl having at least 2 carbon atoms); and compounds of the form $\phi_n(I,S)(P,Sb,As)F_m$, where n is 2 or 3 and m is 4 for P and 6 for Sb or As. In selecting a particular compound, there are these considerations:

Since the response to time-temperature exposure generally depends on the extent of photoactivation, it is important that the photoacid generator either not respond to ambient light exposure or that the indicator be protected from such exposure (e.g., by incorporating an opaque cover sheet or by keeping the indicator in the dark). In addition, the photoactivation step must be reproducible. That can be accomplished conveniently and easily by, for example, using a reproducible light source or monitoring the photoactivation exposure. An advantage of the present indicators is that leuco base systems develop no substantial coloration, even with exposure to radiation considerably in excess of the amount required for photoactivation.

Wavelengths in the visible range are convenient to use for activation, but they can also cause problems. If time-temperature exposure is monitored by changes in reflection density, then it is important that the light whose reflection is being measured not be capable of causing additional activation. Since it is convenient to use visible-light reflection, preferably there should be no activation at wavelengths longer than 400 nm. Thus, a material activatable at wavelengths in the range between about 200 nm and 400 nm is preferred.

A photoreaction that could easily be driven to completion might be desirable, since the resultant activation could be relatively independent of precise radiation dose. However, in the preferred embodiment of the present indicator, a higher level of photoactivation yields an indicator that responds (i.e., darkens) more rapidly at a given temperature. Thus, in that case, a single material can serve as an indicator over a wide range of time and temperature depending on the extent of photoactivation.

The photoacid should be thermally stable in the application environment; i.e., it should not be thermally activatable.

A preferred photoacid generator is o-nitrobenzaldehyde (ONB), which undergoes efficient photochemical conversion to the corresponding nitrosobenzoic acid:

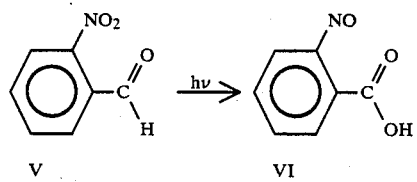

V     VI

Compared with normal aliphatic carboxylic acids ($pK_a \sim 4.8$), benzoic acids are strong acids ($pK_a \sim 4.2$) and benzoic acids that are orthosubstituted with electron withdrawing groups are stronger yet (o-nitrobenzoic acid, $pK_a \sim 2.2$; o-chlorobenzoic acid, $pK_a \sim 2.9$). Thus, o-nitrosobenzoic acid (VI) is a strong acid relative to aliphatic carboxylic acids.

An alternative to ONB for the photosensitive compound is 2,2,2-tribromoethanol ($CBr_3CH_2OH$). This compound generates HBr when it is exposed to UV light. However, compared with a system using ONB, a similarly photoactivated 2,2,2-tribromoethanol system responds more slowly at a given temperature. Therefore, ONB is preferred.

A practical time-temperature indicator of the present invention comprises a mixture of leuco base and photoacid dispersed in a medium and coated onto a substrate. Preferably, the medium comprises a polymer, such as polyvinyl alcohol (PVA), polyvinyl acetate (PVAc), or mixtures of the two. PVAc is preferred, because it is more soluble than is PVA in organic solvents, such as alcohol/water mixtures. Since leuco base and ONB are also soluble in organic solvents, good quality PVAc coatings can be prepared. Generally, the greater the alcohol concentration in an alcohol/water solvent, the more rapid is the time-temperature-induced color change in the coating prepared from it. About 95% alcohol is a practical maximum, because PVAc is not soluble in 100% alcohol. An indicator that comprises malachite green leuco base and ONB dispersed in PVAc is preferred.

Any suitable method may be used to apply an indicator to a substrate, including spraying (e.g., with an airbrush) or coating with a doctor knife or Mayer rod. Depending on the coating method used, it may be necessary to control the viscosity of the solution by, for example, the molecular weight of the polymer medium. Any suitable substrate can be used for the coating, including paper, thermoplastics, metal, etc. Paper is preferred because it is inexpensive and easy to use. Faster color change can be achieved by using thicker coatings, which can be prepared, for example, by making multiple coatings on a single area. The combined influence on rate of color change of coating thickness and degree of photoactivation permit a single indicator composition to monitor the freshness of products whose shelf lives differ from each other by a factor of more than 30.

An optional cover sheet that prevents unwanted photoactivation can also provide an oxygen barrier, which is useful for indicators that develop color when exposed to oxygen. Finally, a cover sheet can protect the coating and thereby prevent damage to the coating during handling. Polyester is one of many materials that are suitable for cover sheets.

The following examples are presented in order to provide a more complete understanding of the invention. The specific techniques, conditions, materials, and reported data set forth to illustrate the principles and practices of the invention are exemplary and should not be construed as limiting the scope of the invention.

EXAMPLE 1

60 mg of malachite green leuco [p,p'-benzylidenebis(N,N-dimethylaniline], purchased from Fisher Scientific Company, was placed in 1 ml of organic solvent. (Alcohol, acetone, and chloroform were each used in separate tests, with similar results.) The solution was then mixed with 30 mg of o-nitrobenzaldehyde (ONB) crystals. Pieces of filter paper were dipped in the resulting solution. The coated pieces appeared faint grey and remained so for days when stored in the dark. However, by irradiating with UV light for a few seconds, the strips were "activated" and developed a very faint green color. The photoactivated samples, when left at different temperatures (room temperature, refrigeration temperature, etc.), developed more green color at different rates.

EXAMPLE 2

An aqueous medium (gel) was prepared by heating a mixture of 4 g polyvinyl alcohol (PVA) in 100 ml water at 80° C. for a few minutes. The PVA (from Aldrich) had a molecular weight of 115,000 and was 99–100% hydrolyzed. 1 mL of the PVA gel and 60 mg of malachite green leuco were mixed well by grinding together. Strips of filter paper 12.5 mm×100 mm were coated with the above mix either by using a Mayer rod or through a silk screen and were then dried at room temperature in a dark hood. 15 mg of ONB (photoacid generator) were dissolved in 1 mL of reagent ethanol. Dried coated strips, 12.5×6.3 mm, were briefly soaked with the ONB solution and were laminated as follows: A coated strip was thermally sealed between two sheets of transparent, heat-sealable polyester film (100 micrometer thickness, obtained from Kapak Corp) to form a "label". Initial reflectivity ranged from 95–99%. Some of these labels were stored in the dark at room temperature and some were stored at refrigeration temperature for time-temperature monitoring of the unactivated labels. Photoactivation of the other labels was accomplished by irradiating individual labels with a 100 W mercury arc lamp for a specific period of time (from 5–20 seconds). The polyester film filtered out light having a wavelength shorter than 300 nm. After photoactivation, the reflectivities ranged from 85–90% (still looked virtually colorless).

A decrease in reflectance with time at a constant temperature was monitored using an optical scanning wand that employs 632 nm light to measure the reflectivity of an indicator label relative to a standard (reference) bar code. In practice, a rectangular hole was cut in a bar code label and the indicator label was placed under the hole. The wand scanned both the bar code label and indicator label, as the two labels were held together. Over a period of time, the reflectivity of the indicator label decreased at a temperature-dependent rate. Typical plots are shown in FIG. 1 for room temperature (22° C.) and refrigeration temperature (6° C.). All reflectivity values are averages of at least ten scans. The unactivated labels were also monitored for a period of more than a month, and no color development was observed either at 6° C. or at room temperature. Using crystal violet leuco instead, in the same system, the final color developed was violet. Similarly, blue color appeared when a mixture of leuco bases of malachite green and crystal violet was used in the proportion of 5:1, respectively.

EXAMPLE 3

Polymeric gels were prepared from 10% polyvinyl acetate (PVAc-M.W. 120,000, Aldrich) solutions in different mixtures of alcohol and water, the alcohol content ranging from 60% to 90%. Mixtures of 300 mg leuco base (malachite green) and 25 mg ONB in 10 ml of each of these polymeric gels were coated on Whatman #41 filter papers using a Paasche airbrush. The coated samples were dried in a dark hood for 4 hours and then laminated and photoactivated by the methods of Example 2. The rates of color development of the activated labels at room temperature and at 6° C. were measured by the method of Example 2. The rate of color development scaled with the alcohol content—fastest for samples prepared in 90% alcohol and slowest for samples prepared in 60% alcohol.

EXAMPLE 4

Using the procedure in Example 3, a coating mix was prepared by blending together leuco base, ONB and PVAc gel prepared in an alcohol/water mixture. Pieces of filter paper were coated by spraying the coating mixture with a Paasche airbrush. Several samples were prepared with 2 or more coatings of the same material. The coated strips were dried and laminated. After photoactivation, the reflectivity at 632 nm was monitored while the samples were stored at refrigeration temperature (6° C.) and the results appear in FIG. 2. Samples A and B each had one coat of coating mixture, but they had different periods of photoactivation. More activation resulted in a faster rate of change in reflectivity. Samples C and D each had two coats; again rates varied according to photoactivation period. Samples E and F were prepared by applying a third coat on top of two coats. Again, the rates varied with photoactivation period. Immediately after photoactivation, the reflectivities (R) of the samples ranged from 85–90%; however, for simplicity, all starting points are shown to be 87% in FIG. 2.

EXAMPLE 5

A polymeric gel was prepared by placing 10 g polyvinyl acetate (m.w. 120,000) in 100 ml of a mixture of alcohol and water (75% alcohol) and heating the mixture at 80° C. for two hours. A coating mix was prepared by blending together 300 mg leuco base (malachite green) and 25 mg ONB in 10 ml of this polymeric gel. The mix was air-brushed through a slit onto a blank section of a bar code label. The coating thickness was adjusted by controlling the number of passes of the airbrush over the slit. The coated bar code label was dried inside a hood and stored in the dark. The coated area was activated by a 10-second UV light exposure. To prevent further photoactivation by ambient light, the coated area was covered with a UV-absorbing plastic strip. Color development in the label was monitored by scanning directly across the activated bar code label.

Coating directly onto a blank section of a bar code label has a clear advantage over systems that require encapsulation in that straightforward printing techniques can be used to apply the indicator material.

I claim:

1. A photoactivatable time-temperature indicator, comprising a mixture of
   (a) a thermally inactive compound that comprises a leuco base and
   (b) a photosensitive compound that, on exposure to actinic radiation, forms an acid that converts the leuco base to a thermally active product.

2. A photoactivatable time-temperature indicator, comprising a mixture of
   (a) a thermally inactive compound that comprises a leuco base and
   (b) a photosensitive compound that, on exposure to actinic radiation, forms an acid that converts the leuco base to a thermally active product, wherein said mixture is dispersed in a medium and coated onto a substrate.

3. The indicator of claim 2 in which the thermally inactive compound comprises one or more leuco bases of triarylmethane dyes.

4. The indicator of claim 3 in which the leuco bases include at least one selected from the group consisting of malachite green leuco, brilliant green leuco, and crystal violet leuco.

5. The indicator of claim 4 in which the leuco bases include malachite green leuco.

6. The indicator of claim 3 in which the photosensitive compound is o-nitrobenzaldehyde or 2,2,2-tribromoethanol.

7. The indicator of claim 2 in which the medium comprises a polymer.

8. The indicator of claim 7 in which the medium comprises polyvinyl alcohol.

9. The indicator of claim 7 in which the medium comprises polyvinyl acetate.

10. The indicator of claim 2 in which the substrate comprises paper.

11. The indicator of claim 2 further comprising a cover sheet.

12. The indicator of claim 11 in which the cover sheet comprises polyester.

13. A method of measuring an incremental time-temperature exposure, which comprises the steps:
   (a) exposing a photoactivatable indicator comprising a mixture of a thermally inactive compound which includes essentially a leuco base and a photosensitive compound which on exposure to actinic radiation forms an acid that converts the leuco base to a thermally active product, to actinic radiation to render said indicator thermally active,
   (b) measuring the reflectivity of the indicator at a specified wave length,
   (c) measuring the reflectivity of the indicator at the specified wave length after the incremental time-temperature environmental exposure, and
   (d) calculating the incremental time-temperature exposure by using a pre-established relationship between a change in reflectivity of the indicator and time-temperature exposure.

14. The method of claim 13 in which the photoactivatable indicator is a mixture of o-nitrobenzaldehyde, malachite green leuco, and polyvinyl acetate.

15. The method of claim 13 in which the actinic radiation is electromagnetic radiation having a wavelength in the range between about 200 nm and about 400 nm.

16. The method of claim 13 in which the temperature exposure is in the range between about $-20°$ and $60°$ C.

17. A method of measuring an incremental time-temperature exposure of a perishable article by
   (a) applying to the article an indicator comprising a mixture of a thermally inactive compound that includes essentially a leuco base and a photosensitive compound which on exposure to actinic radiation forms an acid that converts the leuco base to a thermally active product,
   (b) exposing the indicator to actinic radiation to render it thermally active,
   (c) measuring the reflectivity of the indicator at a specified wavelength,
   (d) measuring the reflectivity of the indicator at the specified wavelength after incremental time-temperature exposure, and
   (e) calculating the incremental time-temperature exposure by using a pre-established relationship between a change in reflectivity of the indicator and time-temperature exposure.

* * * * *